(12) United States Patent
Pannell et al.

(10) Patent No.: US 7,726,585 B2
(45) Date of Patent: Jun. 1, 2010

(54) EXTERNAL CHEMICAL DISTRIBUTION SYSTEM AND METHOD

(75) Inventors: Shane D. Pannell, Mesa, AZ (US); Michael K. Wrigley, Phoenix, AZ (US)

(73) Assignee: Perimicon, LLC, Chandler, AZ (US)

( * ) Notice: Subject to any disclaimer, the term of this patent is extended or adjusted under 35 U.S.C. 154(b) by 659 days.

(21) Appl. No.: 10/783,169

(22) Filed: Feb. 19, 2004

(65) Prior Publication Data

US 2005/0184170 A1    Aug. 25, 2005

(51) Int. Cl.
*B05B 3/00*    (2006.01)
(52) U.S. Cl. .............. 239/208; 239/266; 239/269; 141/231; 141/279; 141/319; 141/382; 137/236.1; 137/615
(58) Field of Classification Search ............... 239/208, 239/266–269; 169/48, 16; 141/206, 319, 141/279, 382–389, 231; 137/615, 236.1, 137/363, 372
See application file for complete search history.

(56) References Cited

U.S. PATENT DOCUMENTS

| | | | | |
|---|---|---|---|---|
| 1,235,657 A | * | 8/1917 | Coles | 239/266 |
| 2,749,180 A | * | 6/1956 | Andrews | 239/450 |
| 2,862,765 A | * | 12/1958 | Wing | 239/303 |
| 4,175,703 A | * | 11/1979 | Valiant | 239/208 |
| 4,674,685 A | | 6/1987 | Ford | |
| 4,862,931 A | * | 9/1989 | Vella | 141/1 |
| 4,944,110 A | | 7/1990 | Sims | |
| 5,165,482 A | * | 11/1992 | Smagac et al. | 169/45 |
| 5,231,796 A | | 8/1993 | Sims | |
| 5,347,749 A | | 9/1994 | Chitwood et al. | |
| 5,378,086 A | | 1/1995 | Campbell, Jr. et al. | |
| 5,819,466 A | | 10/1998 | Aesch et al. | |
| 6,434,880 B1 | | 8/2002 | DuBois et al. | |
| 6,446,383 B1 | | 9/2002 | Hoshall | |
| 6,463,694 B1 | | 10/2002 | Manciet | |
| 6,493,987 B1 | | 12/2002 | Aesch, Jr. et al. | |
| 6,564,504 B2 | | 5/2003 | Hoshall | |

* cited by examiner

*Primary Examiner*—Christopher S Kim
(74) *Attorney, Agent, or Firm*—Robert D. Atkins

(57) ABSTRACT

A chemical distribution system affixes flexible tubing (50) along exterior surfaces (52) of a dwelling (12) and along structures (16) external to the dwelling. The tubing is attached to the exterior surfaces with clamps (54) and exposed for maintenance. The clamps are form-fitted to the tubing. Spray nozzles (58) are inserted into the openings in the tubing for dispensing a chemical solution. The openings can be preformed or cut into solid tubing at during installation. A connector (42) has one end coupled to a hose for receiving the chemical solution and another end coupled to the tubing. The fixed distribution system provides for precise and even application of the chemical solution with minimal operator intervention.

16 Claims, 5 Drawing Sheets

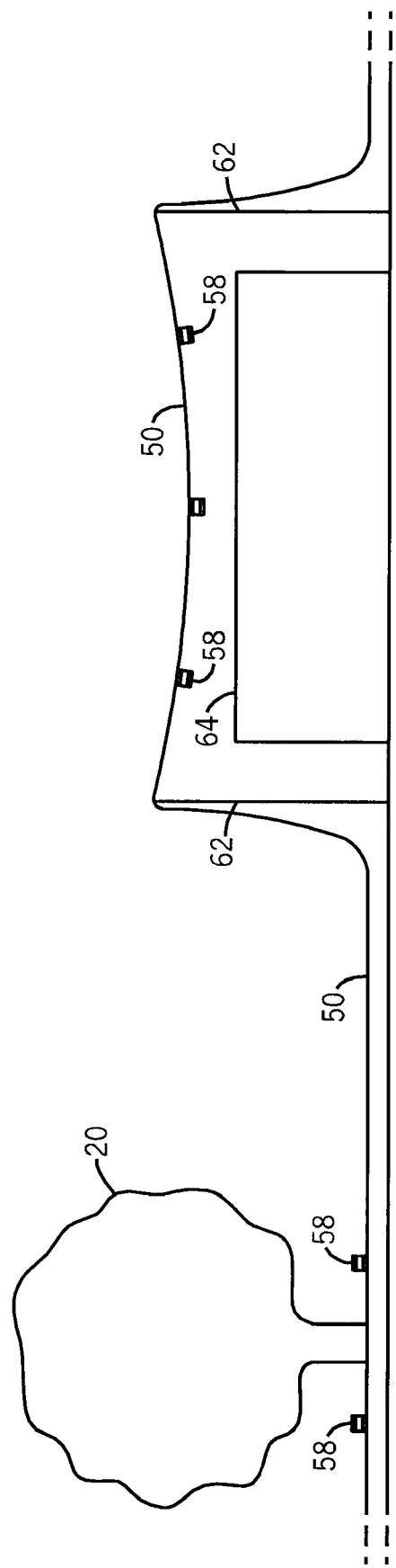

EXTERNAL CHEMICAL DISTRIBUTION SYSTEM AND METHOD

FIELD OF THE INVENTION

The present invention relates in general to chemical distribution systems and, more particularly, to a chemical distribution system affixed to structures which are external to dwellings.

BACKGROUND OF THE INVENTION

Chemicals are commonly used in a myriad of applications to control pests and disease. Chemical agents are also used to apply fertilizer to landscape plants, gardens, and crops. Chemical pesticides rid dwellings and open areas from potentially damaging and annoying pests such as ants, roaches, scorpions, crickets, termites, mites, tics, and other insects. These insects are known to spread disease, destroy vegetation, invade dwellings, infest food supplies, sting or bite people, and bother pets. Chemical herbicides are useful to rid lawns, gardens, and flowerbeds from unsightly weeds. Chemical fertilizers provide vital nutrients to plants of all varieties.

There exist a number of methods and apparatus, which are used to apply or dispense chemical mixtures. Inside dwellings, chemicals have been applied with aerosol cans, hand-pump sprayers, back-pack sprayers, and other mobile pressurized containers. It is known to install fixed chemical distribution systems inside the walls and foundation of structures for subterranean pests, e.g., termites. As for open areas, such as yards, gardens, greenbelts, parks, and fields, the chemical pesticides are typically applied from back-pack sprayers or pumped from a truck and applied using a pressurized hose. A volume of chemical mixture is held in a storage tank on the truck. The hose is reeled from the back of the truck. The storage tank is pressurized to force the chemical solution through the hose. The operator drags the hose around from place to place and hopefully sprays the chemical pesticide in the proper concentration to the necessary locations to rid the open areas of unwanted pests.

For exterior application, hand-held sprayers and back-pack sprayers hold relatively small amounts of chemical mixture and require significant time to cover large areas. Moreover, it is easy to get uneven or inconsistent application and coverage with portable sprays and even entirely miss certain areas through misjudgment or neglect. Some areas are hard to get to with manual sprayers. Using the pressurized hose method delivers more chemical per unit time and generally receives a much greater volume of available mixture from the storage tank. However, the power hose has its own drawbacks. There is set-up time to inspect the application area, pressurize the tank, and deploy the hose. The hose is heavy and requires substantial effort to drag around. In warm climates, the heat is a real problem when performing such hard physical labor. Dragging the hose in and around buildings, corners, trees, plants, furniture, fountains, pools, and other outside structures can cause damage to the hose as well as the yard. Plants get uprooted, furniture gets knocked over, gravel gets displaced, hose contacts pool water, and owners get annoyed. The use of pressurized hoses is still no assurance of consistent and even application of the chemical, either because certain areas are inaccessible or through improper application. Some areas are under-sprayed and some areas are over-sprayed. Constant exposure to and breathing of the chemical spray and mist can be harmful to the long-term health of the operator. The use of power hoses still involves entering the application area and possibly having to deal with hostile dogs.

A need exists for a more convenient and efficient means of applying chemical agents to outside open areas.

SUMMARY OF THE INVENTION

In one embodiment, the present invention is a chemical distribution system comprising a first portion of tubing affixed along an exterior surface of a dwelling. A second portion of tubing is affixed along structures external to the dwelling. The second portion of the tubing is connected to the first portion of tubing. A plurality of outlets is coupled to the first and second portions of tubing for dispensing a chemical solution. A connector has a first end coupled for receiving the chemical solution and a second end coupled to the first or second portions of tubing.

In another embodiment, the present invention is a method of dispensing a chemical solution comprising the steps of connecting a source of chemical solution to one end of a tubing which is affixed to exterior surfaces, wherein the tubing including outlets, and pumping the chemical solution through the tubing to dispense the chemical solution through the outlets.

BRIEF DESCRIPTION OF THE DRAWINGS

FIG. 5 illustrates the flexible tubing routed along the ground and suspended over structures in the open areas.

DETAILED DESCRIPTION OF THE DRAWINGS

Figure 1:
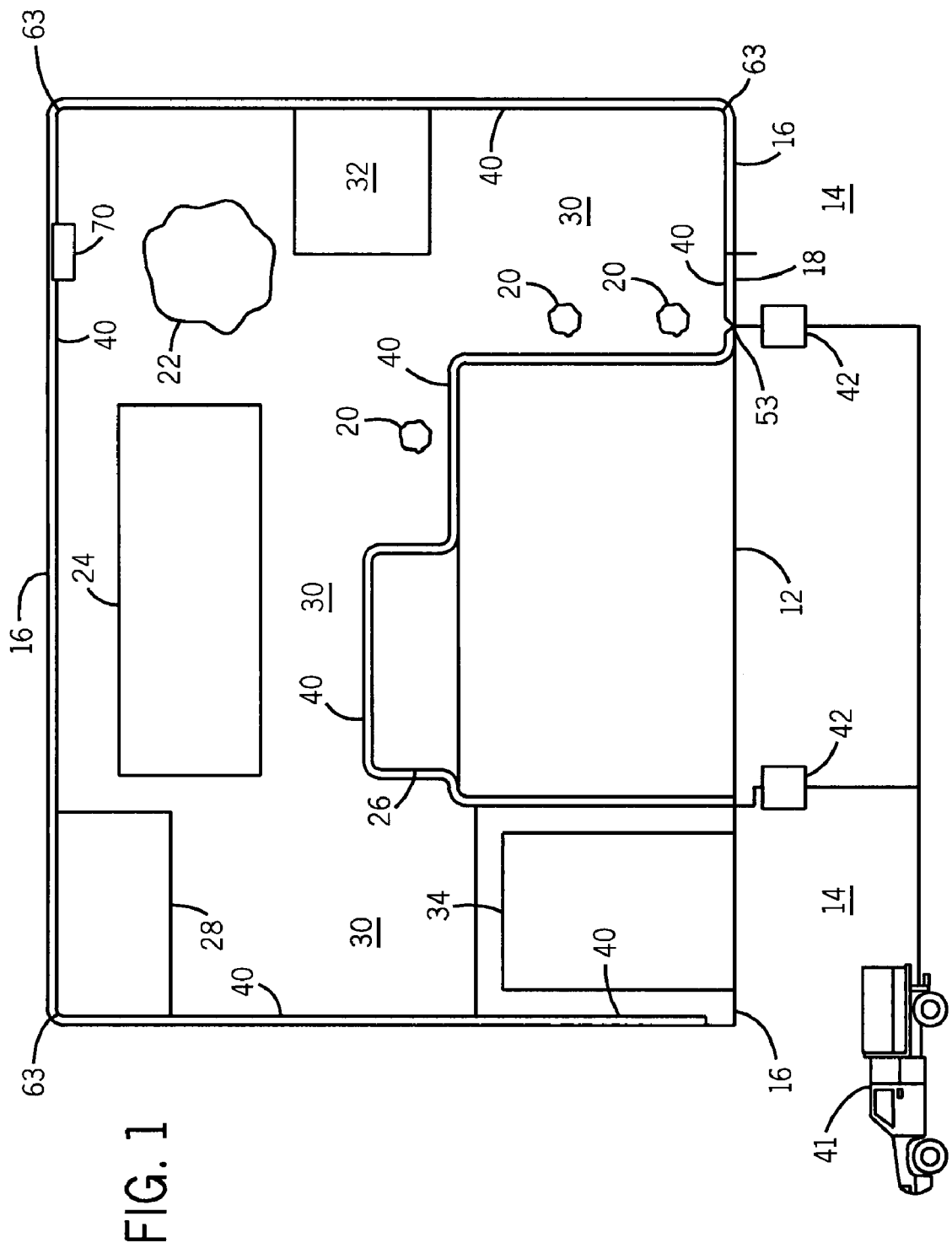
FIG. 1 illustrates a dwelling and outside open areas.

Referring to FIG. 1, a building structure or dwelling 12 is shown located on a property. Building structure 12 could be a residential home, school, church, retail store, industrial park, or large industrial campus. Many building structures have outside open areas within the property boundaries. The open areas around building structure 12 contain a number of features and structures such as yards, grass, gravel beds, landscaping, trees, shrubs, flowerbeds, arboretums, gazebos, sidewalks, patios, pools, ponds, gardens, parking pads, play areas, fences, and the like.

The open areas outside building structure 12 exist as natural or semi-natural settings having exposure to insects, small animals, and other pests. The ground areas are also subject to accumulation of weeds, which can be unsightly to the landscape investment. The property owner typically wants to reduce or minimize the infestation of unwanted pests and weeds in and around the open areas of the property. Accordingly, the owner will spray or have sprayed chemical pesticides and herbicides in and around the open areas of the property to kill and eliminate the pests and weeds. In addition, the property owner may want to apply chemical fertilizers to provide important nutrients to the existing vegetation. In other applications, there may be a need to apply animal retardants, vegetation pre-emergence, and other chemical mixtures in an effort to protect and maintain the quiet enjoyment of the property.

The chemical mixtures, such as pesticides and other pest control agents, must be applied in the correct concentration and to the proper areas to be effective. It is important to properly and adequately cover all open areas with the chemical pesticide; otherwise, insects will continue to live in areas left unprotected or under-sprayed. On the other hand, overspraying is unnecessary, costly, wasteful, and potentially harmful to the environment.

As shown in FIG. 1, the outside open areas of building structure 12 include front yard 14, fence 16, gate 18, shrubs 20, tree 22, swimming pool 24, patio 26, garden 28, grass areas 30, play area 32, and concrete pad 34, collectively external structures 36. A chemical distribution system 40 is installed in and around the outside open areas of building structure 12. Chemical distribution system 40 is intended for external applications, i.e., for spraying chemicals in and around external structures 36. Once installed, chemical distribution system 40 requires little time and effort to use and maintain. The chemical operator saves time and money and can pass value onto the property owner.

Chemical distribution system 40 includes a connector or hookup port 42. The chemical application technician arrives with a truck 41 containing the chemical solution, for example, a pesticide. The technician connects a high-pressure, chemical application hose reeled from the truck to connector or port 42. Once connected, the technician need no longer drag the chemical application hose around the property. Connector 42 can be enclosed in a connector box or junction box buried in the ground at a convenient access location on the property. For the present discussion, the junction box is located just outside fence 16 near gate 18. The technician removes a lid from the junction box to gain access to connector 42. Connector 42 may be horizontally or vertically oriented and mounted within the junction box. The application hose is maneuvered to make connection to connector 42. Connector 42 can also be contained within an enclosure or junction box attached to building structure 12. Connector 42 has a quick-connect fitting for the application hose, or a conventional threaded coupling.

Figure 2:
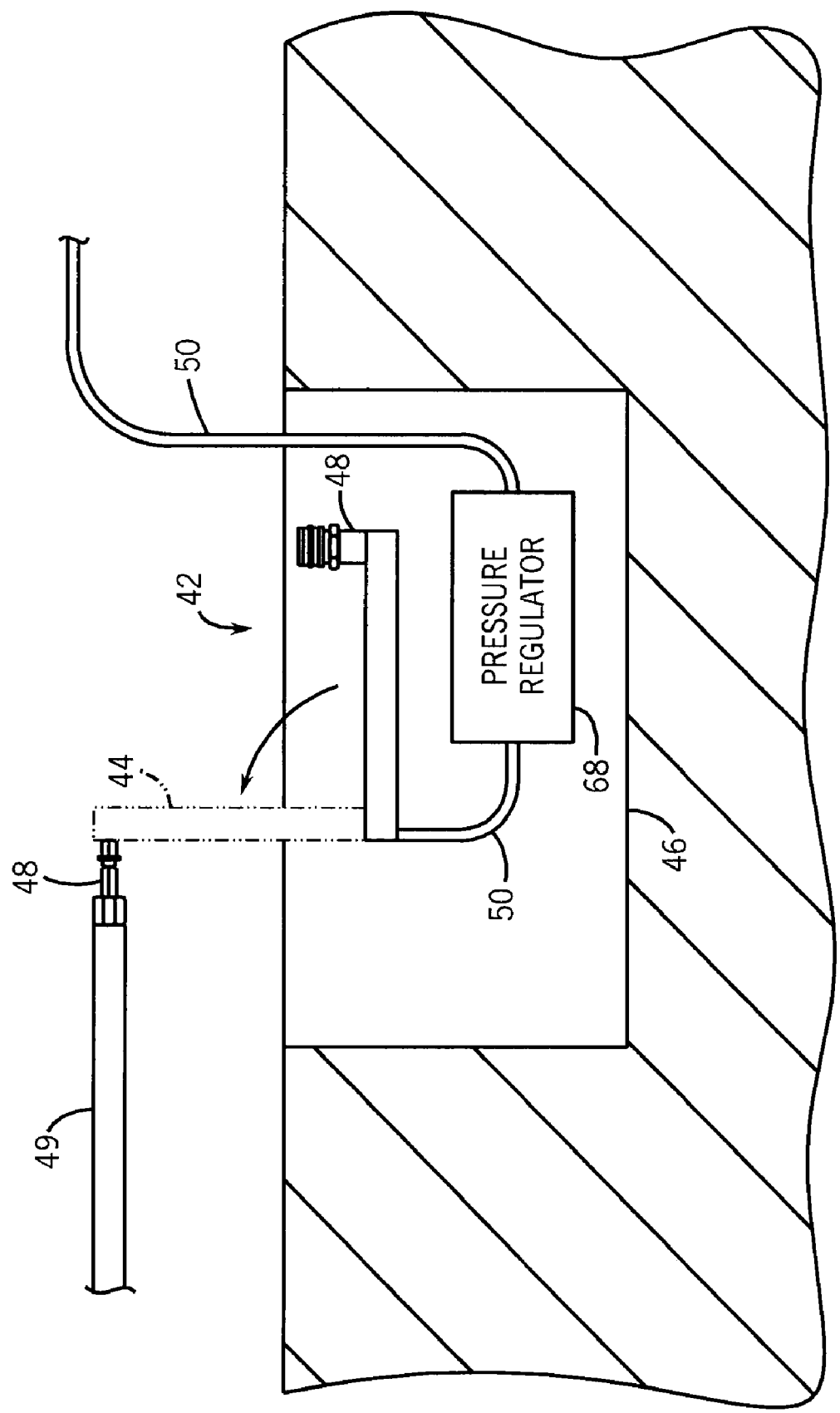
FIG. 2 illustrates the junction box for the connector with rotating lever-arm.

In another embodiment, as shown in FIG. 2, connector 42 may include a lever-arm 44 laid lengthwise within junction box 46 when not in use and which rotates 90 degrees to a vertical position to provide easy connection without unduly bending or kinking chemical application hose 49. Junction box 46 is placed in the ground. Quick-connect fitting 48 is attached to one end of lever-arm 44 for connecting to chemical application hose 49. The other end of lever-arm 44 connects to tubing 50.

Tubing 50 is a flexible, round tubing, hose, or piping which is routed in and around the outside open areas of the property. Tubing 50 is intended to be substantially exposed, i.e., laid above ground and exterior to building structure 12. Tubing 50 is made with chemical resistant material such as polyethylene, polyurethane, nylon, or polypropylene with a pressure rating of 60 PSI or higher. Tubing 50 comes in a variety of diameters, e.g., ⅛ inch inside diameter (ID) to ¾ inch ID and ¼ inch outside diameter (OD) to 1 inch OD, and may be pre-drilled with holes or punch hole openings spaced at regular intervals. The pre-formed holes can be spaced 1-20 inches apart depending on application. Tubing 50 is also available as solid tubing with regular spaced locations for insertion points to be made in the tubing. That is, the tubing walls are made thinner at the pre-defined insertion points to aid in forming the holes. Alternatively, the installer can use a punch or cutting tool to create holes at any location along the solid tubing 50. The punch or tube cutter in often the tool of choice as it provides the most flexibility and efficiency in selecting locations to form the holes.

Figure 3:
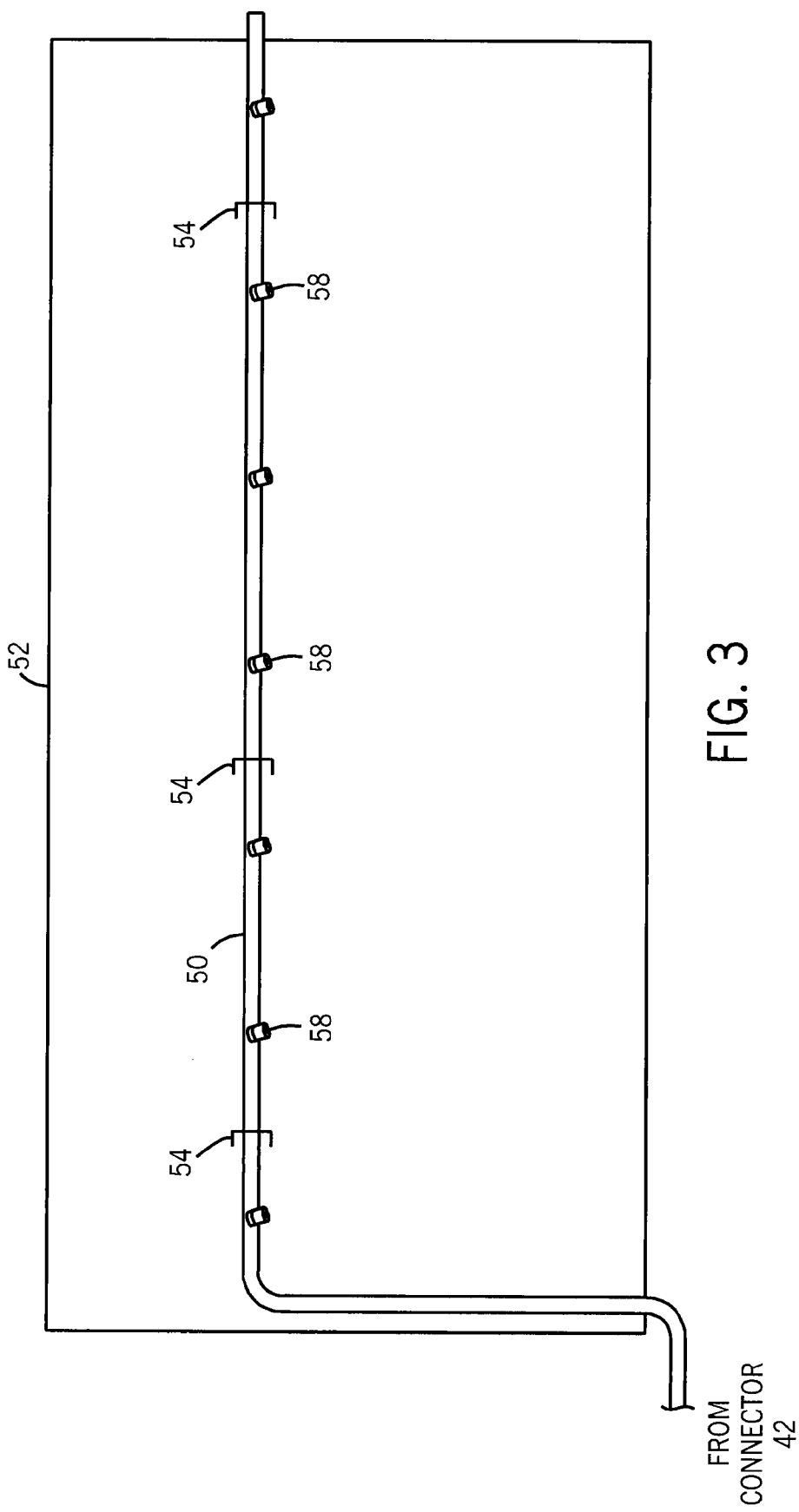
FIG. 3 illustrates the flexible tubing affixed to exterior surfaces of the dwelling.

From connector 42, tubing 50 is routed along foundation wall 52 of building structure 12 as shown in FIG. 3. Tubing 50 is attached to foundation wall 52 with U-shaped clamps 54 and self-taping concrete screws. It is understood that other mounting devices such as insulated or rubber coated P shaped clamps also may be used to install the tubing. Clamps 54 are spaced 5-7 feet apart as necessary to reduce sagging in tubing 50. In another embodiment, clamps 54 include a molded, plastic portion in the shape of a partial circular form. Clamps 54 are attached to foundation wall 52 and the round tubing 50 snaps into the molded form with a pressure fit. Tubing 50 is located external to building structure 12 for ease of installation, inspection, and maintenance. The installer holds tubing 50 up to foundation wall 52 and secures the tubing to the vertical wall with clamps 54. Tubing 50 may be tucked-up under a lip or offset from building structure 12 to remove it from line-of-sight, but the tubing remains exposed for ready and easy access to inspection and maintenance needs.

The tubing 50 installed along foundation wall 52 may come pre-drilled with holes spaced at regular intervals. Alternatively, the installer may place solid tubing 50 along foundation wall 52, and then manually punch holes at selected locations with the punch tool. A spray nozzle or outlet 58 is inserted into each hole of tubing 50 along foundation wall 52 for dispensing and applying the chemical pesticide to the open target areas proximate to building structure 12 along foundation wall 52. The tubing 50 may have the outlets 58 pre-formed or integral to the tubing. The spray nozzle 58 includes an aperture through which the spray is directed and controlled. The selected locations for punch holes depend upon the pesticide manufacturer's recommended application instructions and any external structures 36 adjacent to or in proximity of foundation wall 52 that could interfere with the spraying pattern or otherwise unnecessarily be exposed to the chemical pesticide. The spray nozzles 58 are inserted into tubing 50 along foundation wall 52 for an even, complete, and directed coverage of the chemical pesticide to the outside ground areas proximate to building structure 12, in accordance with government regulations and manufacturer's recommendations. In one scenario, spray nozzles 58 are inserted into tubing 50 every 15 inches with breaks to avoid direct spray of the chemical pesticide on existing plants and other external structures 36 along foundation wall 52 which are not intended to be sprayed. The chemical solution applied to the target area will kill and eliminate the insects and pests in the open areas where the pesticide is applied.

The spray nozzles 58 are typically a non-corrosive metal such as brass or stainless steel and can be circular or cylindrical in shape with an aperture for releasing the chemical spray. The apertures of different nozzles can be set to have different flow rates and spray patterns. The aperture can be large or small and have "+" opening, circular opening, or rectangular opening. In some embodiments, the aperture opening is adjustable to provide a controllable, variable spray in terms of flow rate and pattern by rotating the nozzle head.

Connector 42, tubing 50, clamps 54, and spray nozzles 58 are integral components of chemical distribution system 40. Chemical distribution system 40 is a fixed system installed throughout the property at specific locations for dispensing the chemical pesticide precisely where it is needed, and not applying the chemical in areas where it is not needed or wanted. The chemical application technician visits the property at regular intervals, e.g., monthly. Upon arrival, the technician connects the chemical application hose 49 to connector 42. The chemical pesticide is pumped through the fixed chemical distribution system 40 and precisely applied with the proper concentrations to the desired locations. When the pesticide application is complete, the technician purges the lines and tubing with air. The process is fast, simple, and accurate.

Figure 4:
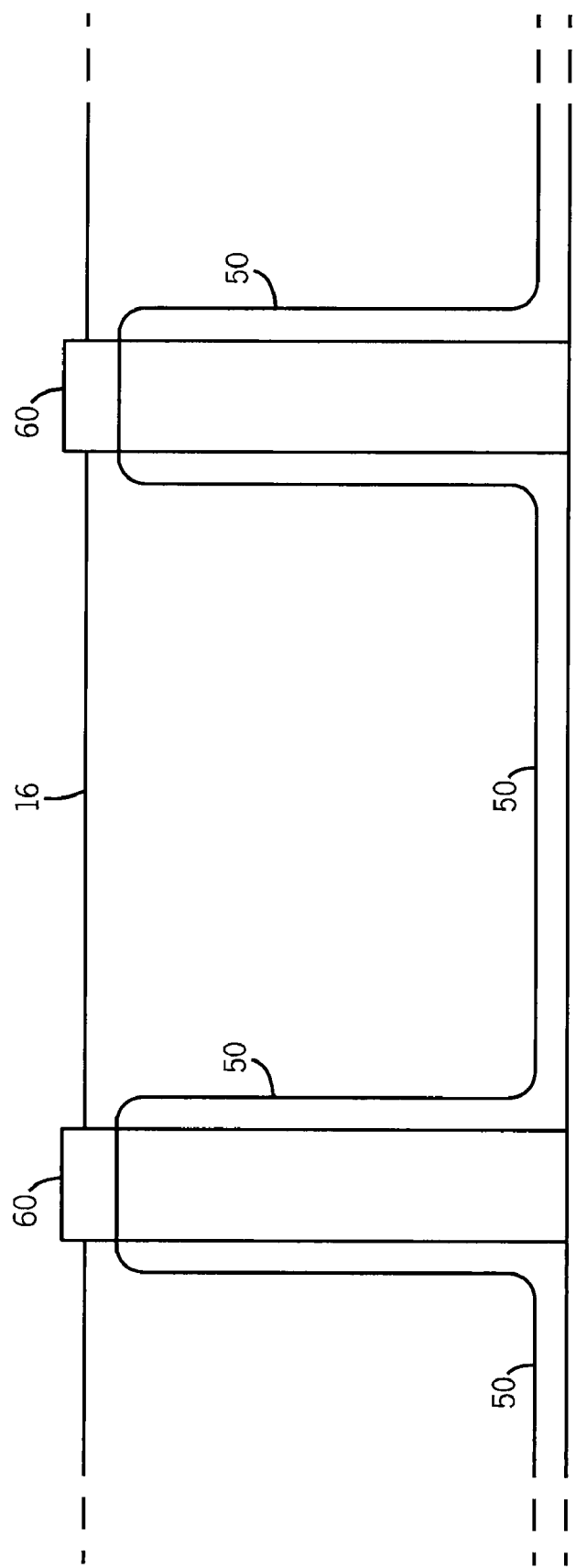
FIG. 4 illustrates the flexible tubing affixed to a fence external to the dwelling.

Returning to FIG. 1, from connector 42, just inside fence 16, chemical distribution system 40 splits with a portion running along foundation wall 52 of building structure 12 and a portion running along fence 16. A "Y" coupling or "T" coupling 53 can be used to split tubing 50. Tubing 50 runs along side fence 16, past play area 32 to the corner of the fence behind tree 22. Fence 16 may be cinder block or wood construction. As shown in FIG. 4, fence 16 typically contains a number of posts or pillars 60 regularly spaced about 10-15 feet apart for supporting the main body of the fence. The cracks and crevices of the posts and pillars of fence 16 are prime insect infestation sites. To increase the effectiveness of chemical distribution system 40, tubing 50 is routed up and down the posts and pillars 60 of fence 16.

Some of the tubing 50 installed along side fence 16 is pre-drilled with holes spaced at regular intervals. In addition, the installer may place solid tubing 50 in the vicinity of play area 32, and then manually punch holes with the punch tool at selected locations. The property owner may not want any pesticide sprayed in and around play area 32. A spray nozzle or outlet 58 is inserted into each hole of tubing 50 along side fence 16 for dispensing and applying the chemical pesticide to the open areas proximate to the fence. The locations selected for punch holes depend upon the pesticide manufacturer's recommended application instructions and any external structures 36 adjacent to or in proximity of fence 16 that could interfere with the spraying pattern or otherwise would be unnecessarily exposed to the chemical pesticide. The spray nozzles 58 are inserted into the holes of tubing 50 along side fence 16 for an even, complete, and directed coverage of the chemical pesticide to the outside ground areas proximate to side fence 16, in accordance with government regulations and manufacturer's recommendations. In one scenario, spray nozzles 58 are installed every 15 inches with breaks to avoid direct spray of the chemical pesticide on existing plants and other external structures 36 along side fence 16 which are not intended to be sprayed.

An elbow connector 63 can be used for tubing 50 to turn the corner of the fence behind tree 22. Otherwise, tubing 50 is sufficiently flexible to bend 90 degrees between the side and back fence 16. Tubing 50 then runs along back fence 16, past pool 24, to the corner of the fence near garden 28. Again, tubing 50 is routed up and down the posts and pillars along back fence 16. Some of the tubing 50 installed along back fence 16 is predrilled with holes spaced at regular intervals. In addition, the installer may place solid tubing 50 in the vicinity of pool 24 and garden 28, and then manually punch holes with the punch tool at selected locations with the punch tool. The property owner may not want any pesticide sprayed in and around pool 24 and garden 28. Spray nozzles 58 are inserted into the holes of tubing 50 along back fence 16 for dispensing the chemical pesticide to the open areas proximate to the fence. The locations selected for punch holes depend upon the pesticide manufacturer's recommended application instructions and any external structures 36 adjacent to or in proximity of back fence 16 that could interfere with the spraying pattern or otherwise would be unnecessarily exposed to the chemical pesticide. The spray nozzles 58 are inserted into the holes of tubing 50 along fence 16 for an even, complete, and directed coverage of the chemical pesticide to the outside ground areas proximate to back fence 16. In one scenario, spray nozzles 58 are installed every 15 inches with breaks to avoid direct spray of the chemical pesticide on existing plants and other external structures 36 along back fence 16 which are not intended to be sprayed.

Tubing 50 continues along side fence 16 to the concrete pad 34. Again, tubing 50 is routed up and down the posts and pillars of side fence 16. Tubing 50 installed along side fence 16 is pre-drilled with holes spaced at regular intervals or with solid tubing having holes manually punched at selected locations. Spray nozzles 58 are inserted into the holes of tubing 50 along side fence 16 for dispensing the chemical pesticide to the open areas proximate to the fence.

A second connector 42 is provided near concrete pad 34. The second connector 42 provides another injection point for the chemical pesticide. The tubing 50 from the second connector 42 is routed along the foundation walls of building structure 12 adjacent to concrete pad 34 as described above. The tubing 50 continues around patio 26 and the back of building structure 12 and connects with the tubing running along foundation wall 52. The tubing 50 can also be routed around the end of concrete pad 34 to connect to the tubing on side fence 16. Chemical distribution system 40 thus becomes a closed system with multiple injection points. The closed system may serve to equalize pressure and distribution of the chemical solution. Alternatively, the first connect 42 can inject chemical pesticide into tubing 50 which is then routed to a portion of the property. The tubing 50 is capped off at the end point, for example, at a location along back fence 16. The second connect 42 would inject chemical pesticide into tubing 50 which is then routed to another portion of the property. Again, the tubing 50 is capped off at each end point.

In FIG. 5, tubing 50 can be routed along open ground to apply chemical pesticide to insect-infested areas. Tubing 50 is run along the ground next to shrub 20 and then supported by stakes 62 above external structures 36 such as planter box 64. The stakes 62 use hooks, clamps, or pressure fittings as described above to support and suspend tubing 50. Spray nozzles 58 are inserted into tubing 50 to dispense the chemical pesticide to the intended areas.

The accurate distribution of the chemical pesticide is determined in part by the pressure in tubing 50. A pressure regulator 68 is included in junction box 46 as shown in FIG. 2. Pressure regulator 68 insures that the desired pressure is maintained on tubing 50 throughout the property. In larger systems, it may be necessary or desirable to use additional or intermediate pressure regulators and booster pumps at various points of the property to maintain the necessary tubing pressure at all points of the system. A pressure regulator and booster pump 70 is shown in FIG. 1 at the back end of the property such a purpose.

A feature of chemical distribution system 40 is the ease of use and maintenance. Once installed, the system is efficient and effective to use. The technician connects the chemical application hose 49 to connector 42, sets the storage tank pressure in the truck, and begins pumping. The pesticide can be pumped through tubing 50 in liquid, mist, or gaseous state. The pesticide is dispensed from spray nozzles 58 onto the intended areas, in a concentration and coverage consistent with the manufacturer's recommendations and compliant with government regulations. The chemical pesticide is thus distributed through fixed chemical distribution system 40 and applied with the proper concentrations to the desired external locations of the property to kill and eliminate insects and pests. The same process is applicable to weed control and fertilizer application. The technician's involvement is usually limited to connecting the application hose to connector 42, setting the storage tank pressure, and monitoring the spray volume and time. Otherwise, for the most part, chemical distribution system 40 is self-regulating. The process requires minimal judgment and action by the technician. The property owner and chemical application company owner have greater confidence that the pesticide is being properly applied and thoroughly distributed. The application process is more efficient, accurate, and requires much less time than manual application methods.

Occasionally, the technician will want to visually inspect the tubing 50 and nozzles 58 to insure that chemical distribution system 40 is operating properly and that the chemical pesticide is being dispensed as intended. If a defective portion is found, the tubing 50 can be repaired with a splice or replacement section. If nozzles 58 become plugged or defective, they can be replaced or cleaned out with a simple wire tool. Once the spray application is complete, the system is purged with pressurized air or other innocuous agent. No pesticide or residue is left in the tubing or nozzles.

Chemical distribution system 40 is a time-saver and provides accurate, measured, and consistent coverage of the pesticide or other chemical solutions. The pest control dispensing system improves the efficiency and effectiveness of pesticide or other pest control agent application, providing a more complete barrier of defense as compared to manual application methods. The fixed distribution system provides for precise and even application of the chemical solution with minimal operator intervention. The effectiveness is further evident by the ability of chemical distribution system 40 to apply pesticide to target areas that are difficult to reach via manual application, such as behind bushes and other structures. The technician can accurately monitor the quantity of pesticide being applied.

Chemical distribution system 40 may be routed into the interior area of a garage, storage shed, or other enclosed structure. However, the same principals remain of keeping the tubing accessible for ease of installation, inspection, and maintenance.

A person skilled in the art will recognize that changes can be made in form and detail, and equivalents may be substituted for elements of the invention without departing from the scope and spirit of the invention. The present description is therefore considered in all respects to be illustrative and not restrictive, the scope of the invention being determined by the following claims and their equivalents as supported by the above disclosure and drawings.

What is claimed is:

1. A chemical distribution system, comprising:
   a residential home;
   a yard in an exposed area adjacent to the residential home including a fence, gate, shrub, tree, swimming pool, patio, garden, grass area, play area, and concrete pad;
   a hollow tubing disposed around each of a plurality of target areas in the yard including the fence, shrub, tree, garden, and grass area, the tubing transporting a chemical solution selected from the group consisting of pesticides, herbicides, fertilizers, animal retardants, and vegetation pre-emergence, the tubing being made of a chemical resistant material selected from the group consisting of polyethylene, polyurethane, nylon, and polypropylene, with a pressure rating of at least sixty pounds per square inch, the tubing having an inside diameter ranging from one-eighth inch to three-fourth inch and an outside diameter ranging from one-fourth inch to one inch, the tubing having a plurality of openings cut through its wall structure at selected points in accordance with government regulations and manufacturer's recommendations and corresponding to each of the plurality of target areas, the tubing including a plurality of "Y" and elbow couplings for changing direction of the tubing to cover the plurality of target areas, the tubing being routed up and down structures that extend vertically above ground secured with pressure-fit clamps and otherwise laid above ground;
   a plurality of spray nozzles inserted into the openings in the tubing for distributing the chemical solution to the selected target areas, the spray nozzles being circular in shape, made of non-corrosive metal and having adjustable flow rates and spray patterns;
   a truck for transporting the chemical solution to the residential home, the truck including a hose for transporting the chemical solution to the tubing;
   first and second junction boxes disposed below ground in a front area of the residential home;
   a first pressure regulator connected to the tubing within the first junction box for regulating pressure of the chemical solution;
   a first hook-up port disposed within the first junction box and having an output connected to a first end of the tubing, the first hook-up port including a lever arm which lays horizontal within the junction box when not in use and rotates ninety degrees to a vertical position so that a fitting on an end of the lever arm extends above ground when connected to the hose from the truck;
   a second hook-up port disposed within the second junction box and having an output connected to a second end of the tubing, the second hook-up port including a lever arm which lays horizontal within the junction box when not in use and rotates ninety degrees to a vertical position so that a fitting on an end of the lever arm extends above ground when connected to the hose from the truck, wherein the first and second hook-up ports form a closed system to equalize pressure and distribution of the chemical solution;
   a second pressure regulator coupled in a portion of the tubing which is located in a rear portion of the yard for regulating pressure of the chemical solution; and
   a booster pump coupled in a portion of the tubing which is located in the rear portion of the yard for increasing the pressure of the chemical solution.

2. The chemical distribution system of claim 1, wherein the tubing is supported by stakes at selected target areas.

3. The chemical distribution system of claim 1, wherein the plurality of spray nozzles is disposed about fifteen inches apart.

4. The chemical distribution system of claim 1, wherein the tubing is pre-drilled with punch hole openings spaced at regular intervals one to twenty inches apart for dispensing the chemical solution.

5. A fixed chemical distribution system, comprising:
   a residential home;
   a yard in an exposed area adjacent to the residential home;
   a hollow tubing disposed around each of a plurality of target areas within the yard, the tubing transporting a chemical solution selected from the group consisting of pesticides, herbicides, fertilizers, animal retardants, and vegetation pre-emergence, the tubing being made of a chemical resistant material selected from the group consisting of polyethylene, polyurethane, nylon, and polypropylene, the tubing having a plurality of openings cut through a first portion of its wall structure in accordance with government regulations and Manufacturer's recommendations and a plurality of pre-drilled openings formed in a second portion of the tubing;
   a plurality of spray nozzles inserted into the openings in the first and second portions of the tubing for distributing the chemical solution to the plurality of target areas;

first and second junction boxes disposed below ground in a front area of the residential home;

a first pressure regulator connected to the tubing within the first junction box for regulating pressure of the chemical solution;

a first hook-up port disposed within the first junction box and having an output connected to a first end of the tubing, the first hook-up port including a lever arm which lays horizontal within the junction box when not in use and rotates ninety degrees to a vertical position so that a fitting on an end of the lever arm extends above ground when connected for receiving the chemical solution;

a second hook-up port disposed within the second junction box and having an output connected to a second end of the tubing, the second hook-up port including a lever arm which lays horizontal within the junction box when not in use and rotates ninety degrees to a vertical position so that a fitting on an end of the lever arm extends above ground when connected for receiving the chemical solution, wherein the first and second hook-up ports form a closed system to equalize pressure and distribution of the chemical solution;

a second pressure regulator coupled in a portion of the tubing which is located in a rear portion of the yard for regulating pressure of the chemical solution; and a booster pump coupled in a portion of the tubing which is located in the rear portion of the yard for increasing the pressure of the chemical solution.

6. The fixed chemical distribution system of claim 5, wherein the spray nozzles are circular in shape, made of non-corrosive metal and have adjustable flow rates and spray patterns.

7. The fixed chemical distribution system of claim 5, wherein the tubing includes a plurality of "Y" and elbow couplings for changing direction of the tubing to cover the target areas.

8. The fixed chemical distribution system of claim 5, wherein the tubing is routed up and down structures that extend vertically above ground secured with pressure-fit clamps and otherwise laid above ground.

9. The fixed chemical distribution system of claim 5, further including a truck for transporting the chemical solution to the residential home, the truck including a hose for transporting the chemical solution to the tubing.

10. The fixed chemical distribution system of claim 5, wherein the plurality of spray nozzles are disposed about fifteen inches apart.

11. A chemical distribution system, comprising:

a dwelling;

an exposed area adjacent to the dwelling;

a hollow tubing disposed around each of a plurality of target areas within the exposed area, the tubing transporting a chemical solution selected from the group consisting of pesticides, herbicides, fertilizers, animal retardants, and vegetation pre-emergence, the tubing being made of a chemical resistant material selected from the group consisting of polyethylene, polyurethane, nylon, and polypropylene, the tubing having a plurality of openings cut through a first portion of its wall structure in accordance with government regulations and manufacturer's recommendations and a plurality of pre-drilled openings formed in a second portion of the tubing;

a plurality of spray nozzles inserted into the openings in the first and second portions of the tubing for distributing the chemical solution to the plurality of target areas;

a first junction box disposed below ground in a front area of the dwelling;

a first pressure regulator connected to the tubing within the first junction box for regulating pressure of the chemical solution;

a first hook-up port disposed within the first junction box and having an output connected to a first end of the tubing, the first hook-up port including a lever arm which lays horizontal within the junction box when not in use and rotates ninety degrees to a vertical position so that a fitting on an end of the lever arm extends above ground when coupled for receiving the chemical solution;

a second pressure regulator coupled in a portion of the tubing which is located in a rear portion of the yard for regulating pressure of the chemical solution; and a booster pump coupled in a portion of the tubing which is located in the rear portion of the yard for increasing the pressure of the chemical solution.

12. The chemical distribution system of claim 11, further including:

a second junction box disposed below ground in a front area of the dwelling; and a second hook-up port disposed within the second junction box and having an output connected to a second end of the tubing, the second hook-up port including a lever arm which lays horizontal within the junction box when not in use and rotates ninety degrees to a vertical position so that a fitting on an end of the lever arm extends above ground when coupled for receiving the chemical solution, wherein the first and second hook-up ports form a closed system to equalize pressure and distribution of the chemical solution.

13. The chemical distribution system of claim 11, wherein the spray nozzles are circular in shape, made of non-corrosive metal and have adjustable flow rates and spray patterns.

14. The chemical distribution system of claim 11, wherein the tubing includes a plurality of "Y" and elbow couplings for changing direction of the tubing to cover the target areas.

15. The chemical distribution system of claim 11, wherein the tubing is routed up and down structures that extend vertically above ground secured with pressure-fit clamps and otherwise laid above ground.

16. The chemical distribution system of claim 11, further including a truck for transporting the chemical solution to the residential home, the truck including a hose for transporting the chemical solution to the tubing.

* * * * *